US011523992B2

(12) United States Patent
Jain et al.

(10) Patent No.: US 11,523,992 B2
(45) Date of Patent: *Dec. 13, 2022

(54) PROCESS FOR PREPARING FILLED HARD-SHELL CAPSULES WITH (METH)ACRYLATE COPOLYMER BASED COATINGS WITH A CAPSULE-FILLING MACHINE

(71) Applicant: Evonik Operations GmbH, Essen (DE)

(72) Inventors: Vinay Jain, Mumbai (IN); Ashish Guha, Mumbai (IN); Shraddha Joshi, Thane (IN); Felix Hofmann, Darmstadt (DE); Bettina Hölzer, Bensheim (DE); Hans Bär, Michelstadt (DE)

(73) Assignee: Evonik Operations GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/595,145

(22) PCT Filed: Apr. 29, 2020

(86) PCT No.: PCT/EP2020/061872
§ 371 (c)(1),
(2) Date: Nov. 10, 2021

(87) PCT Pub. No.: WO2020/229178
PCT Pub. Date: Nov. 19, 2020

(65) Prior Publication Data
US 2022/0142930 A1    May 12, 2022

(30) Foreign Application Priority Data

May 15, 2019  (IN) .............................. 201941019448

(51) Int. Cl.
*A61K 9/48* (2006.01)
(52) U.S. Cl.
CPC .......... *A61K 9/4816* (2013.01); *A61K 9/4891* (2013.01)
(58) Field of Classification Search
CPC ............................ A61K 9/4816; A61K 9/4891
See application file for complete search history.

(56) References Cited

U.S. PATENT DOCUMENTS

| 4,138,013 A | 2/1979 | Okajima |
| 2003/0060381 A1 | 3/2003 | Meier et al. |
| 2021/0361585 A1 | 11/2021 | Guha et al. |

FOREIGN PATENT DOCUMENTS

| JP | S61221117 | 10/1986 | |
| JP | 2003325642 | 11/2003 | |
| WO | 0168767 | 9/2001 | |
| WO | 2008/135090 | 11/2008 | |
| WO | 2011/012369 | 2/2011 | |
| WO | WO-2013170012 A2 * | 11/2013 | ........... A61K 31/568 |
| WO | 2015/177028 | 11/2015 | |
| WO | 2019/096833 | 5/2019 | |

OTHER PUBLICATIONS

A.A. Attama, "*Polyelectrolyte Complexes of Eudragit L30 D-55 and Gelatin: Antinociceptive Activity of Entrapped Piroxicam*", Drug Delivery, vol. 14, 2007, pp. 155-162.
Cole, et al., "*Enteric coated HPMC capsules designed to achieve intestinal targeting*", International Journal of Pharmaceutics, vol. 231, 2002, pp. 83-95.
European Search Report dated Feb. 28, 2020 in European Application No. 19198015.0, 6 pages.
Huyghebaert, et al., "*Alternative method for enteric coating of HPMC capsules resulting in ready-to-use enteric-coated capsules*", European Journal of Pharmaceutical Sciences, vol. 21, XP-002560461, 2004, pp. 617-623.
International Search Report dated Aug. 3, 2020 in PCT/EP2020/061872, 4 pages.
Lu, et al., *Dissolution of Gelatin Capsules: Evidence and Confirmation of Cross-Linking*, Dissolution Technologies, Aug. 2017, 16 pages.
Written Opinion dated Aug. 3, 2020 in PCT/EP2020/061872, 6 pages.
U.S. Appl. No. 17/438,886, filed Sep. 13, 2021, Hölzer et al.
U.S. Appl. No. 17/595,147, filed Nov. 10, 2021, Jain et al.
U.S. Office Action dated Jun. 14, 2022, in U.S. Appl. No. 15/733,083, 12 pages.

* cited by examiner

*Primary Examiner* — Robert A Wax
*Assistant Examiner* — Olga V. Tcherkasskaya
(74) *Attorney, Agent, or Firm* — Grüneberg and Myers PLLC

(57) ABSTRACT

A process can be used for preparing a polymer coated hard-shell capsule, filled with a fill containing a biologically active ingredient. The hard-shell capsule contains a body and a cap, and in a closed state, the cap overlaps the body either in a pre-locked state or in a final-locked state. The material of the body and the cap contains an ethyl-, methyl-, or propyl-ether of cellulose, starch, or pullulan. The hard-shell capsule is coated with a coating layer that covers the hard-shell capsule in the pre-locked state. The coating layer contains one or more (meth)acrylate copolymers, where the coating layer is present in an amount of about 1 to 5.8 mg/cm². The process involves providing the polymer-coated hard-shell capsule in the pre-locked state to a capsule-filling machine, separating the body and the cap, filling the body with the fill, and rejoining the body and the cap in the final-locked state.

14 Claims, 1 Drawing Sheet

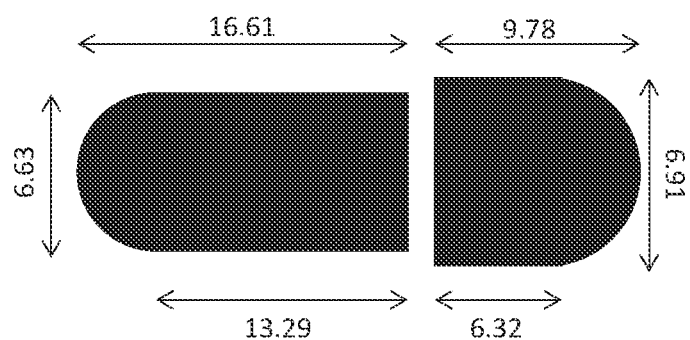

PROCESS FOR PREPARING FILLED HARD-SHELL CAPSULES WITH (METH)ACRYLATE COPOLYMER BASED COATINGS WITH A CAPSULE-FILLING MACHINE

CROSS-REFERENCE TO RELATED APPLICATIONS

This application is the National Stage entry under § 371 of International Application No. PCT/EP2020/061872, filed on Apr. 29, 2020, and which claims the benefit of priority to Indian Application No. 201941019448, filed on May 15, 2019. The content of each of these applications is hereby incorporated by reference in its entirety..

BACKGROUND OF THE INVENTION

Field of the Invention

The invention is in the field of processes for preparing filled polymer-coated hard-shell capsules with a capsule filling machine.

Description of Related Art

U.S. Pat. No. 4,138,013 describes hard-shell capsules with enteric properties. The hard-shell capsules comprise telescopically engaged body and cap portions. The capsule body and cap portions are formed by dip-molding using a homogeneous film-forming mixture, comprising polymers selected from hydroxypropyl methyl cellulose (HPMC), a mixture of (1) hydroxypropyl methyl cellulose and an ammonium salt of cellulose acetate phthalate or (2) gelatin and an ammonium salt of a copolymer of (meth)acrylic acid and methacrylic acid alkyl ester. The capsules itself have already enteric properties without applying a further enteric coating layer.

Xujin Lu and Pankaj Shah, "Dissolution of Gelatin Capsules: Evidence and Confirmation of Crosslinking" in Dissolution technologies August 2017, 6-20. The authors discuss that crosslinking is a common problem in the dissolution of gelatin capsules.

A. A. Atama (2007) "Polyelectrolyte Complexes od EUDRAGIT® L30 D-55 and Gelatin, Antinociceptive Activity of Entrapped Piroxicam". The author discusses the interaction of EUDRAGIT® L 30 D-55 and gelatin. EUDRAGIT® L 30 D-55 is a 30% aqueous dispersion of an anionic copolymer based on methacrylic acid and ethyl acrylate. Gelatin type A is generated by acid pretreatment of pig skin. The isoelectric point (IEP) of gelatin is between 7-9. Below pH 8 gelatin A is positively charged and can interact with negatively charged EUDRAGIT® L 30 D-55.

Huyghebaert et al., *European Journal of Pharmaceutical Sciences* 21 (2004) 617-623, describe an alternative method for the enteric coating of capsules made of HPMC in which ready-to-use enteric capsule parts are obtained. It is reported that, in contrast to gelatine capsules, HPMC capsules can be enteric coated relatively easily from aqueous preparations. However, it is necessary to additionally apply a sealing between the capsule halves, e.g. through a gelatine solution to be applied manually, in order to avoid a leakage of the capsule and an uncontrolled escape of the contents in the stomach. Another technique is to apply water/ethanol mixtures between the capsule halves and to weld the parts together at 40-60° C. Using aqueous preparations (EUDRAGIT® FS 30 D, EUDRAGIT® L 30 D-55) based on (meth)acrylate copolymers or polyvinyl acetate phthalate, plasticizers such as triethyl citrate and further auxiliaries, such as, for example, talc, it is possible to provide HPMC capsules with an enteric film from separately coated bodies and caps. A separate sealing step can be prevented in the case of this formulation process. In particular, HPMC capsules which have been coated with (meth)acrylate copolymers are depicted as particularly advantageous in the sum of their properties.

WO 2011/012369A1 describes a coating composition for the enteric coating of capsule halves made of water-soluble or water-swellable polymer material.

JP2003-325642A describes a hard, empty capsule with enteric solubility and a manufacturing method for such a hard, empty capsule. The capsule cap is coupled with the capsule body in the semi-locked state and an enteric solubility membrane is formed on the entire surface. Then the capsule cap is removed from the capsule body and the contents are fill-packed. The parts are then coupled in a locked state. This allows to avoid the application of a coating after the filling of the capsule, which would add a thermal burden to the content. Also, a seal sticker sealing of the capsule after filling can be avoided, since there is an overlap of the coating in the locked state, which seals the gap between the capsule cap and capsule body. The capsule may be filled with the desired content such as propolis, raw royal jelly, black-vinegar extract. The capsules as described are made from gelatin by a dip coating procedure by immersing metallic molds into a gelatin and water dispersion. The metallic molds are pulled up, rotated, cooled and dried. Thereby, cylindrical membranes are formed in uniform thickness, cut in the dimensions as required as a capsule caps or as capsule bodies. Capsule caps and capsule bodies are coupled in a semi-locked state. An enteric soluble substance may be applied by spray coating.

The enteric soluble substance according to JP2003-325642A may be a plant or animal protein originating in wheat, a soybean, a collagen, gelatin, etc., cellulose-acetate phthalate, a cellulose acetate succinate, cellulose acetate maleate, hydroxypropyl methyl cellulose phthalate, hydroxypropyl-methylcellulose acetate succinate, polyvinyl-acetate phthalate, polyvinyl butyrate phthalate. The amount of coating is more than the quantity performed by conventional enteric solubility capsule formation, 20 to 80 by weight %, 40 to 60 by weight % desirable. The film thickness is about 0.1 to about 0.5 mm. These film thicknesses are larger than the tolerance variation of the outer diameter of the capsule body and the internal diameter of the capsule cap.

JP S61-221117A describes an enteric hard capsule formation to be used, for example, in the medical field. The capsules are coated in a pre-locked state before filling to avoid the drawbacks of conventional hard capsules coated with enteric solvent after filling, e.g. losses of expensive medicines. The coating in the pre-locked state results in a partial overlap of the body with the cap that has a sufficient bucking effect to prevent gastric juices from entering into the capsule from the fitting part of the cap and the body. The invention uses ordinary gelatin capsules that may be of the so-called locking method of "snap-fit". As enteric solvents hydroxypropyl methyl cellulose phthalate, hydroxypropyl methyl cellulose acetate phthalate, cellulose acetate phthalate and methacrylic acid-methyl methacrylate copolymers may be used. In the examples capsules of size No. 1 were coated with 14 and 38 mg hydroxypropyl methyl cellulose phthalate (HP-55, Shin-Etsu Chemical Co., Ltd). It was found that 18 mg per capsule with a film thickness of around 80 μm was preferable. JP S61-221117A mentions methacrylic acid-methyl methacrylate copolymers as further possible coatings.

Hard-shell capsules which are enteric coated in a pre-locked state, opened, filled with a fill and are then closed to a final-locked state are in principle known from JP2003-325642A and JP S61-221117A. Both citations describe the use of gelatin capsules which tend to cross linking during storage (Xujin Lu and Pankaj Shah, "Dissolution of Gelatin Capsules: Evidence and Confirmation of Crosslinking" in Dissolution technologies August 2017, 6-20). The gelatin capsules are pre-coated with a coating zein (JP2003-325642A) or hydroxypropyl methyl cellulose acetate phthalate (HP-55 JP2003-325642A).

The use of enteric coated capsules in a pre-locked state seems to be advantageous since the application of additional sealing steps as discussed in Huyghebaert et al. (European Journal of Pharmaceutical Sciences 21 (2004) 617-623) can be avoided. Also, a thermal burden for the fill that takes place when the coating is applied after the filling, can be avoided by means of coating in the pre-locked state before capsule filling.

For industrial scale production a high turnover and output process is desirable. Such high turnover and output can be achieved by use of automated capsule-filling machines. Half and fully automated capsule filling machines can process provided capsules which are already coated in the pre-locked state and rapidly perform the steps of separating the body and the cap, filling the body with the fill and rejoining the body and the cap in the final-locked state. A fully automated machine is capable to run at a speed of 1,000 or even a much more higher number of processed capsules per hour. The high speed however causes high mechanical stress to the pre-locked capsules and especially to the mechanical resistance of the coatings. Therefore, there is a need to provide a process, which allows the processing of capsules coated in a pre-locked state in a capsule filling machine without impairing properties such as resistance in acidic medium (less than 10% active ingredient release at pH 1.2 in 120 min) and rapid dissolution at higher pH (pH 5.5 or above, pH 6.8).

SUMMARY OF THE INVENTION

The invention is concerned with a process for preparing a polymer coated hard-shell capsule, filled with a fill comprising a biologically active ingredient, wherein the hard-shell capsule is comprising a body and a cap, wherein in a closed state the cap overlaps the body either in a pre-locked state or in a final-locked state, wherein the material of the body and the cap comprises an ethyl-, methyl- or propyl-ether of cellulose, starch or pullulan, wherein the hard-shell capsule is coated with a coating layer that covers the hard-shell capsule in the pre-locked state, wherein the coating layer is comprising one or more (meth)acrylate copolymer(s), wherein the coating layer is present in an amount of about 1 to 5.8 mg/cm$^2$, preferably 2 to 5 mg/cm$^2$, wherein a dried film with a thickness of 250 μm, corresponding to the composition of the coating layer, shows an elongation at break of about 15 to 500, preferably 50 to 450%, wherein the polymer-coated hard-shell capsule is provided in the pre-locked state to a capsule-filling machine, which performs the steps of separating the body and the cap, filling the body with the fill and rejoining the body and the cap in the final-locked state.

BRIEF DESCRIPTION OF THE DRAWING

The Figure shows a schematic drawing of the body (left) and the cap (right) of a Vcaps® Plus size 1 hard-shell capsule with the relevant dimensions in mm.

DETAILED DESCRIPTION OF THE INVENTION

Biologically Active Ingredient

The process as disclosed refers to a polymer coated hard-shell capsule, filled with a fill comprising a biologically active ingredient. A biologically active ingredient may be defined as an ingredient that may after delivery or intake confers a preventive or therapeutical effect in an animal or human body. The biologically active ingredient is preferably a pharmaceutically active ingredient and/or a nutraceutically active ingredient.

Pharmaceutically or Nutraceutically Active Ingredients

The invention is preferably useful for immediate, enteric or sustained release formulated pharmaceutical or nutraceutical dosage forms with a fill-in of pharmaceutically or nutraceutically active ingredients.

Suitable therapeutic and chemical classes of pharmaceutically active ingredients which members may be used as fill-in for the described polymer-coated hard-shell capsules are for instance: analgesics, antibiotics or anti-infectives, antibodies, antiepileptics, antigens from plants, antirheumatics, benzimidazole derivatives, beta-blocker, cardiovascular drugs, chemotherapeutics, CNS drugs, digitalis glycosides, gastrointestinal drugs, e.g. proton pump inhibitors, enzymes, hormones, liquid or solid natural extracts, oligonucleotides, peptide hormones proteins, therapeutic bacteria, monoclonal microbials, microbial components, peptides, proteins and their (metal)salts i.e. aspartates, chlorides, orthates, urology drugs, vaccines.

Further examples of drugs that may be used as fill-in for the described polymer-coated hard-shell capsules are for instance acamprosat, aescin, amylase, acetylsalicylic acid, adrenalin, 5-amino salicylic acid, aureomycin, bacitracin, balsalazine, beta carotene, bicalutamid, bisacodyl, bromelain, budesonide, calcitonin, carbamacipine, carboplatin, cephalosporins, cetrorelix, clarithromycin, chloromycetin, cimetidine, cisapride, cladribine, clorazepate, cromalyn, 1-deaminocysteine-8-D-arginine-vasopressin, deramciclane, detirelix, dexiansoprazole, diclofenac, didanosine, digitoxin and other digitalis glycosides, dihydrostreptomycin, dimethicone, divalproex, drospirenone, duloxetine, enzymes, erythromycin, esomeprazole, estrogens, etoposide, famotidine, fluorides, garlic oil, glucagon, granulocyte colony stimulating factor (G-CSF), hepain, hydrocortisone, human growth hormon (hGH), ibuprofen, ilaprazole, insulin, Interferon, Interleukin, Intron A, ketoprofen, lansoprazole, leuprolidacetat lipase, lipoic acid, lithium, kinin, memantine, mesalazine, methenamine, milameline, minerals, minoprazole, naproxen, natamycin, nitrofurantion, novobiocin, oisalazine, omeprazole, orothates, pancreatin, pantoprazole, parathyroidhormone, paroxetine, penicillin, perprazol, pindolol, polymyxin, potassium, pravastatin, prednisone, preglumetacin progabide, pro-somatostatin, protease, quinapril, rabeprazole, ranitidine, ranolazine, reboxetine, rutosid, somatostatin streptomycin, subtilin, sulfasalazine, sulphanilamide, tamsulosin, tenatoprazole, trypsine, valproic acid, vasopressin, vitamins, zinc, including their salts, derivatives, polymorphs, isomorphs, or any kinds of mixtures or combinations thereof.

It is evident to a skilled person that there is a broad overlap between the terms pharmaceutically and nutraceutically active ingredients, excipients and compositions respectively a pharmaceutical or a nutraceutical dosage form. Many substances listed as nutraceuticals may also be used as pharmaceutical active ingredients. Depending on the specific application and local authority legislation and classification, the same substance may be listed as a pharmaceutically or a nutraceutically active ingredient respectively a pharmaceutical or a nutraceutical composition or even both.

Nutraceuticals are well known to the skilled person. Nutraceuticals are often defined as extracts of foods claimed to have medical effects on human health. Thus, nutraceutical active ingredients may display pharmaceutical activities as well: Examples for nutraceutically active ingredients may be resveratrol from grape products as an antioxidant, soluble dietary fiber products, such as psyllium seed husk for reducing hypercholesterolemia, broccoli (sulphane) as a cancer preservative, and soy or clover (isoflavonoids) to improve arterial health. Thus, it is clear that many substances listed as nutraceuticals may also be used as pharmaceutically active ingredients.

Typical nutraceuticals or nutraceutically active ingredients that may be used as fill-in for the described polymer-coated hard-shell capsules may also include probiotics and prebiotics. Probiotics are living microorganisms believed to support human or animal health when consumed. Prebiotics are nutraceuticals or nutraceutically active ingredients that induce or promote the growth or activity of beneficial microorganisms in the human or animal intestine.

Examples for nutraceuticals are resveratrol from grape products, omega-3-fatty acids or (pro)anthocyanines, for instance from blueberries or black currents, as antioxidants, soluble dietary fiber products, such as psyllium seed husk for reducing hypercholesterolemia, broccoli (sulphane) as a cancer preservative, and soy or clover (isoflavonoids) to improve arterial health. Other examples for nutraceuticals are flavonoids, antioxidants, alpha-linoleic acid from flax seed, beta-carotene from marigold petals or anthocyanins from berries. Sometimes the expressions neutraceuticals or nutriceuticals are used as synonyms for nutraceuticals.

Preferred biologically active ingredients are metoprolol, mesalamine and omeprazole.

Polymer Coated Hard-Shell Capsule

The invention is concerned with a process for preparing a polymer-coated hard-shell capsule, comprising a body and a cap. In the closed state the cap overlaps the body either in a pre-locked state or in a final-locked state. The hard-shell capsule is usually commercially available in the pre-locked state and then preferably spray-coated with a coating solution or dispersion comprising one or more (meth)acrylate copolymer(s) to create a coating layer which covers the outer surface of the hard-shell capsule in the pre-locked state.

Hard-Shell Capsules

Hard-shell capsules for pharmaceutical or nutraceutical purposes are well known to a skilled person. A hard-shell capsule is a two-piece encapsulation capsule comprising of the two capsule halves, called the body and the cap. The capsule body and cap material is usually made from a hard and sometimes brittle material. The hard-shell capsule comprises a body and a cap. Body and cap are usually of a one end open cylindrical form with closed rounded hemispherical ends on the opposite end. The shape and size of the cap and body are such that the body can be pushed telescopically with its open end into the open end of the cap.

The body and the cap comprise a potential overlapping matching area (overlap area) outside the body and inside the cap which partially overlap when the capsule is closed in the pre-locked state and totally overlap in the final-locked state. When the cap is partially slid over the overlapping matching area of the body the capsule is in the pre-locked state. When the cap is totally slid over the overlapping matching area of the body the capsule is in the final-locked state. The maintenance of the pre-locked state or of the final-locked state is usually supported by snap-in locking mechanisms of the body and the cap such as matching encircling notches or dimples, preferably elongated dimples.

Usually the body is longer than the cap. The outside overlapping area of the body can be covered by the cap in order to close or to lock the capsule. In the closed state the cap covers the outside overlap area of the body either in a pre-locked state or in a final-locked state. In the final-locked state the cap covers the outside overlap area of the body in total, in the pre-locked state the cap overlaps the outside overlapping area of the body only partially. The cap can be slid over the body to be fixed in usually one of two different positions in which the capsule is closed either in a pre-locked state or in a final-locked state.

Hard-shell capsules are commercially available in different sizes. Hard-shell capsules are usually delivered as empty containers with the body and cap already positioned in the pre-locked state and on demand as separate capsule halves, bodies and caps. The pre-locked hard-shell capsules can be provided to a capsule-filling machine, which performs the opening, filling and closing of the capsules into the final-locked state. Usually hard-shell capsules are filled with dry materials, for instance with powders or granules comprising a biologically active ingredient.

The cap and body are provided with closure means that are advantageous for the pre-locking (temporary) and/or final locking of the capsule.

Therefore, elevated points may be provided on the inner wall of the cap and somewhat larger indented points are provided on the outer wall of the body, which are arranged so that when the capsule is closed the elevations fit into the indentations. Alternatively, the elevations may be formed on the outer wall of the body and the indentations on the inner wall of the cap.

Arrangements in which the elevations or indentations are arranged in a ring or spiral around the wall are also possible. Instead of the point-like configuration of the elevations and indentations, these may encircle the wall of the cap or body in an annular configuration, although advantageously recesses and openings are provided which enable an exchange of gases into and out of the capsule interior.

One or more elevations may be provided in an annular arrangement around the inner wall of the cap and the outer wall of the body such that, in the final-locked position of the capsule, an elevation on the cap is located adjacent to an elevation on the body. Sometimes elevations are formed on the outside of the body close to the open end and indentations are formed in the cap close to the open end such that the elevations on the body latch into the indentations in the cap in the final-locked position of the capsule. The elevations may be such that the cap can be opened in the pre-locked state at any time without damage to the capsule or, alternatively, so that once it has been closed the capsule cannot be opened again without destroying it.

Capsules with one or more such latching mechanisms (latches, for instance two circulating grooves) are preferred. More preferred are capsules with at least two such latching means which secure the two capsule parts to different degrees. In a part of this kind, a first latching (dimples or circulating notches) means may be formed close to the openings in the capsule cap and the capsule body and a second latching (circulating notches) can be shifted somewhat further towards the dosed end of the capsule parts. The first latching means secure the two capsule parts less strongly than the second does. This variant has the advantage that after the production of the empty capsules the capsule cap and capsule body can initially be pre-locked joined together using the first latching mechanism. In order to fill the capsule, the two capsule parts are then separated again. After filling, the two capsule parts are pushed together until the second set of latches firmly secures the capsule parts in a final-locked state.

Preferably, the body and the cap of the hard-shell capsule are comprising each encircling notches and/or dimples in the area, where the cap can be slid over the body. Encircling notches of the body and dimples of the cap match to each other to provide a snap-in or snap into-place mechanism. The dimples may be circular or elongated (oval) in the longitudinal direction.

Encircling notches of the body and encircling notches of the cap (closely matched rings) also match to each other to provide a snap-in or snap into-place mechanism. This allows the capsule to be closed by a snap-into-place mechanism either in a pre-locked state or in a final-locked state.

Preferably, matching encircling notches of the body and elongated dimples of the cap are used to fix the body and the cap to each other in the pre-locked state. Matching encircling notches of the body and the cap are preferably used to fix or lock the body and the cap to each other in the final-locked state.

The area where the cap can be slid over the body may be called the overlapping area of the body and the cap or briefly the overlap area. If the cap overlaps the body only partially, maybe to 20 to 90 or 60 to 85% of the overlap area, the hard-shell capsule is only partially closed (pre-locked). Preferably, in the presence of a locking mechanism, like matching encircling notches and/or dimples in body and cap, the partially closed capsule may be called pre-locked. When the capsule is polymer-coated in the pre-locked state the coating will cover the completely outer surface including that part of the overlap area of the body and cap that is not overlapped by the cap in this pre-locked state. When the capsule is polymer-coated in the pre-locked state and then closed to the final-locked state the coating of that part of the overlap area of the body and cap that was not overlapped by the cap in the pre-locked state will then become covered by the cap. The presence of that part of the coating which is then enclosed in the final-locked state between the body and the cap is sufficient for the hard-shell capsule to be tightly sealed. This was by no means to be foreseen.

If the cap overlaps the total overlapping area of the body, the hard-shell capsule is finally closed or in the final-locked state. Preferably, in the presence of a locking mechanism, like matching encircling notches and/or dimples in body and cap, the finally closed capsule may be called final-locked.

Usually dimples are preferred for the fixing the body and the cap in the pre-locked state. As a non-binding rule the matching area of dimples is smaller than the matching area of encircling notches. Thus snapped-in dimples may be snapped-out again by applying less forces than those that would be necessary to snap-out a snapped-in fixation by matching encircling notches.

The dimples of the body and cap are located in the area where the cap can be slid over the body matching to each other in the pre-locked state by a snap in or snap into-place mechanism. There may be for example 2, 4, or preferably 6 notches or dimples located distributed circular around the cap.

Usually the dimples of the cap and the encircling notches of the body are in the area where the cap can be slid over the body, matching to each other so that they allow the capsule to be closed by a snap-into-place mechanism in the pre-locked state. In the pre-locked state, the hard-shell capsule can be re-opened manually or by a machine without damaging, because the forces needed to open are comparatively low. So, the "pre-locked state" is sometimes designated also as "loosely capped".

Usually the encircling notches or matching locking rings of the body and the cap are in the area where the cap can be slid over the body, matching to each other so that they allow the capsule to be closed by a snap-into-place mechanism in the final-locked state. In the final-locked state, the hard-shell capsule cannot or can be only hardly be re-opened manually or by a machine without damaging, because the forces needed to open are comparatively high.

Usually the dimples and the encircling notches are formed in the capsule body or capsule cap. When the capsule parts provided with these elevations and indentations are fitted into one another, ideally defined uniform gaps of from 10 microns to 150 microns, more particularly 20 microns to 100 microns, are formed along the contact surface between the capsule body and the capsule cap placed thereon.

Preferably, the body of the hard-shell capsule comprises a tapered rim. The tapered rim prevents the rims of the body and the cap to collide and becoming damaged when the capsule is closed manually or by a machine.

In contrast to a hard-shell capsule, a soft-shell capsule is a welded one-piece encapsulation capsule. A soft gel capsule is often made from blow molded soft gelling substances and is usually filled with liquids comprising a biologically active ingredient by injection. The invention is not concerned with welded soft-shell one-piece encapsulation capsules.

Sizes of Hard-Shell Capsules

The polymer coated hard-shell capsule may be derived from an uncoated hard-shell capsule of the standard size 000, 00, 0, 1, 2, 3, 4, 5 or 9.

A closed, final-locked hard-shell capsule may have a total length in the range from about 5 to 40 mm. The diameter of the cap may be in the range from about 4 to 12 mm. The diameter of the body may be in the range from about 2 to 11 mm. The length of the cap may be in the range from about 4 to 20 mm and that of the body in the range from 8 to 30 mm. The fill volume may be about from 0.1 to 2 ml. The difference between the pre-locked length and the final-locked length may be about 1 to 5 mm.

Capsules can be divided into standardized sizes for example from sizes 000 to 5. A dosed capsule of size 000 has, for example, a total length of about 28 mm with an outer diameter of the cap of about 9.9 mm and an outer diameter of the body of about 9.5 mm. The length of the cap is about 14 mm, that of the body about 22 mm. The fill volume is about 1.4 ml.

A closed capsule of size 5 has, for example, a total length of about 10 mm and an outer diameter of the cap of about 4.8 mm and an outer diameter of the body of about 4.6 mm. The length of the cap is about 5.6 mm, that of the body about 9.4 mm. The fill volume is about 0.13 ml.

A size 0 capsule may show a length of about 23 to 24 mm in the pre-locked state and of about 20.5 to 21.5 mm in the final-locked state. Thus, the difference between the pre-locked length and the final-locked length may be about 2 to 3 mm.

Material of the Body and the Cap

The material of the body and the cap comprises an ethyl-, methyl- or propyl-ether of cellulose, starch or pullulan. Cellulose ethers are derivates of cellulose in which the hydrogen atoms of the hydroxyl groups are partially or fully substituted by alkyl groups, such as ethyl-, methyl- or propyl-groups. These derivates of cellulose are well known to a skilled person in pharmacy and galenic. Suitable materials are methyl cellulose (MC), ethyl cellulose (EC), hydroxyethyl cellulose (HEC), hydroxypropyl cellulose (HPC) and/or hydroxypropyl methyl cellulose (HPMC). Preferred is hydroxypropyl methyl cellulose (HPMC).

Coating Layer

The hard-shell capsule is provided in the pre-locked state and spray-coated with a coating solution, suspension or dispersion to create the corresponding coating layer which covers the outer surface of the hard-shell capsule in the pre-locked state.

The coating layer may be a single layer or may comprise or consist of two or more individual layers.

The hard-shell capsule is coated with a coating layer that covers the hard-shell capsule in the pre-locked state. The coating layer is comprising one or more (meth)acrylate copolymer(s), preferably with a glass transition temperature $T_{gm}$ of 125° C. or less (determined by Differential Scanning Calorimetry (DSC) according to ISO 11357-2:2013-05), wherein the coating layer is present in an amount of about 1 to 5.8, preferably 2 to 5 mg/cm, wherein a dried film corresponding to the composition of the coating layer shows an elongation at break of about 15 to 500%. The elongation at break is determined with a test sample (sample type 1B, 20 mm/min) according to DIN EN ISO 527-3:2018, February 2019.

The coating layer, which may be a single layer or may comprise or consist of two or more individual layers, may comprise in total 10 to 100, 20 to 95, 30 to 90% by weight of one or more (meth)acrylate copolymer(s).

The coating layer, which may be a single layer or may comprise or consist of two or more individual layers, may comprise in total 90 to 0, 80 to 5, 70 to 10% by weight of pharmaceutical or nutraceutical excipients.

The one or more (meth)acrylate copolymer(s) and the pharmaceutical or nutraceutical excipients may add up to 100%.

"Duo Coat"

The coating layer may be a single coating layer or may comprise one or two or more individual layers.

An advantageous system comprising a coating layer comprising two individual coatings may comprise an inner coating which comprises a partially neutralized anionic (meth)acrylate copolymer or a water soluble neutral polymer in combination with an outer coating comprising an anionic (meth)acrylate copolymer, which is less neutralized than the material of the inner coating or not neutralized at all (s. WO 2008/135090A1).

Glass Transition Temperature $T_{gm}$

Methacrylic acid-methyl methacrylate copolymers such as EUDRAGIT® L 100 or EUDRAGIT® S 100 show glass transition temperatures $T_{gm}$ of about or somewhat above 150° C. for the EUDRAGIT® L 100 polymer or about or somewhat above 160° C. for the EUDRAGIT® S 100 polymer, which is comparatively high. It should be noted that the $T_{gm}$ of EUDRAGIT® L 100 or EUDRAGIT® S 100 cannot exactly be determined because of the starting decomposition of their functional groups at 150° C. The required elasticity (elongation at break) of the coating layer may be realized by addition of comparatively high amounts of plasticizers and/or emulsifiers and/or detacking agents.

The inventors have found that in a preferred embodiment, a coating layer may comprise one or more (meth)acrylate copolymer(s) with a glass transition temperature $T_{gm}$ of 125° C. or less, preferably from minus 10 to plus 115° C. These polymers are less brittle and more flexible which supports the coating layer to resist against the high mechanical forces occurring during the processing in a capsule filling machine. In combination with these polymers, the required elasticity (elongation at break) of the coating layer may be realized with the addition of less amounts of plasticizers and/or emulsifiers and/or detacking agents. In this embodiment methacrylic acid-methyl methacrylate copolymers may be generally excluded.

Thus, the coating layer may comprise one or more (meth)acrylate copolymer(s) with a glass transition temperature $T_{gm}$ of 125° C. or less, preferably from −10 to 115° C.

Thus, the coating layer may comprise one or more (meth)acrylate copolymer(s) with a glass transition temperature $T_{gm}$ of 125° C. or less, preferably from—10 to 115°, wherein copolymers consisting of polymerized units of methacrylic acid and methyl methacrylate are excluded.

The glass transition temperature $T_{gm}$ is determined by Differential Scanning Calorimetry (DSC) according to ISO 11357-2:2013-05. The determination is performed with a heating rate of 20 k/min.

The glass transition temperature $T_{gm}$ was determined by half step height method as described in section 10.1.2 of DIN EN ISO 11357-2.

Thickness of the Coating Layer

The coating layer is present in an amount of about 1 to 5.8, preferably 2 to 5 mg/cm$^2$. The thickness of the coating layer may be determined by calculation of the amount of the coating material applied to the empty pre-locked capsules, for instance in a spray coating process, in relation to the surface area of the empty pre-locked capsules (see also examples 8 and 9, The Figure). The coating layer may be a single layer or may comprise or consist of two or more individual layers. In the case of two or more individual layers, the thickness of the individual layers cumulating to the thickness of the coating layer in total.

Elongation at Break

The inventors have found that processing in a capsule filling machine requires a certain elasticity of the coating layer. The elasticity of the coating layer may be characterized in that a dried film corresponding to the composition of the coating layer shows an elongation at break of about 15 to 500, preferably 20 to 250%.

Elongation at break may be determined according to DIN EN ISO 527-1: 2012-06 (General principles, especially chapter 8) and 527-3:2018, February 2019, determination of tensile properties for films and sheets with a thickness below 1,000 μm. The elongation at break is the percentage increase in length that a material will achieve before breaking. This figure is shown as the percentage. Suspension of the compositions for the coating layer are spread on a glass plate and dried to a film of 250 μm thickness. The elongation at break is determined with a test sample (sample type 1B, 20 mm/min) according to DIN EN ISO 527-3:2018, February 2019.

Example for the preparation and testing of polymer films:
Formulation:
Polymer dispersion 30 g=9 g solids, used for a 250 μm film after drying.

Equipment:

Glass plate 20 cm×20 cm with a surrounding of 1 cm glass strips of 0.5-0.7 cm height, resulting in a free preparation area of 361 cm. This glass plate is in addition covered with a self-adhesive Polytetrafluoroethylen foil (i.e. Tygaflor®).

Processing:

The polymer and diluent are mixed on a magnetic stirrer for 10 minutes at low speed. The polymer solution or suspension needs to be air free to avoid voids in the polymer foil. The Polytetrafluoroethylen covered glass plate is levelled in an oven and the polymer solution or dispersion is poured into it. The mixture is dried for approximately 4 days at 40° C. After drying the foils or sheets will be conditioned for 16 hours at 23° C. and 50% relative humidity.

The resulting film thickness is approx. 250 µm.

The same method can be used to manufacture films of coating suspensions. In this case the coating suspension is prepared like usually (e.g. using an ultra turrax). An aliquot amount for 9 g of total solids (including formulation excipients) is diluted with demineralized water up to a total amount of 100 g.

(Meth)Acrylate Copolymer(s)

The coating layer may comprise a (meth)acrylate copolymer selected from copolymers comprising polymerized units of methacrylic acid and ethyl acrylate, of methacrylic acid and methyl methacrylate, of ethyl acrylate and methyl methacrylate or of methacrylic acid, methyl acrylate and methyl methacrylate, from a mixture of a copolymer comprising polymerized units of methacrylic acid and ethyl acrylate with a copolymer comprising polymerized units of methyl methacrylate and ethyl acrylate and a mixture of a copolymer comprising polymerized units of methacrylic acid, methyl acrylate and methyl methacrylate with a copolymer comprising polymerized units of methyl methacrylate and ethyl acrylate.

The coating layer may comprise a (meth)acrylate copolymer comprising polymerized units of 40 to 60% by weight of methacrylic acid and 60 to 40% by weight of ethyl acrylate (type EUDRAGIT® L 100-55). A suitable second polymer is EUDRAGIT® L 100-55 (Evonik Nutrition & Care GmbH, Darmstadt, Germany), which is a copolymer comprising polymerized units of 50% by weight of methacrylic acid and 50% by weight of ethyl acrylate. EUDRAGIT® L 30 D-55 is a 30% by weight aqueous dispersion of EUDRAGIT® L 100-55. The glass transition temperature $T_{gm}$ of EUDRAGIT® L 100-55 is about 110° C.

The coating layer may comprise a (meth)acrylate copolymer comprising polymerized units of 5 to 15% by weight methacrylic acid, 60 to 70% by weight of methyl acrylate and 20 to 30% by weight methyl methacrylate (type EUDRAGIT® FS). A suitable copolymer is EUDRAGIT® FS which is a copolymer polymerized from 25% by weight of methyl methacrylate, 65% by weight of methyl acrylate and 10% by weight of methacrylic acid. EUDRAGIT® FS 30 D is a dispersion comprising 30% by weight EUDRAGIT® FS. The glass transition temperature $T_{gm}$ of EUDRAGIT® FS is about 45° C.

The coating layer may comprise a (meth)acrylate copolymer comprising polymerized units of 60 to 80% of ethyl acrylate and 40 to 20% by weight of methyl methacrylate (type EUDRAGIT® NE or the type EUDRAGIT® NM). EUDRAGIT® NE and EUDRAGIT® NM are copolymers comprising free-radically polymerized units of 28 to 32% by weight of methyl methacrylate and 68 to 72% by weight of ethyl acrylate. The glass transition temperature $T_{gm}$ of EUDRAGIT® NE is about minus 8° C.

The coating layer may comprise a (meth)acrylate copolymer comprising polymerized units of 40 to 60% by weight of methacrylic acid and 60 to 40% by weight of methyl methacrylate (type EUDRAGIT® L 100). EUDRAGIT® L 100 is a copolymer polymerized from 50% by weight of methyl methacrylate and 50% by weight of methacrylic acid. The glass transition temperature $T_{gm}$ of EUDRAGIT® L 100 is about or somewhat above 150° C.

The coating layer may comprise a (meth)acrylate copolymer comprising polymerized units of 20 to 40% by weight of methacrylic acid and 60 to 80% by weight of methyl methacrylate (type EUDRAGIT® S 100). EUDRAGIT® S 100 is a copolymer polymerized from 70% by weight methyl methacrylate and 30% by weight methacrylic acid. The glass transition temperature $T_{gm}$ of EUDRAGIT® S 100 is about or somewhat above 160° C.

Mixtures of (Meth)Acrylate Copolymers

The coating layer may comprise a mixture of (meth)acrylate copolymers of the above-mentioned type EUDRAGIT® L 100-55 and of type EUDRAGIT® NE or type EUDRAGIT® NM. The glass transition temperature $T_{gm}$ of EUDRAGIT® NE and EUDRAGIT® NM is about −8° C.

Type EUDRAGIT® NE or type EUDRAGIT® NM (meth)acrylate copolymers are (meth)acrylate copolymers comprising polymerized units of 60 to 80% of ethyl acrylate and 40 to 20% by weight of methyl methacrylate. EUDRAGIT® NE and EUDRAGIT® NM are copolymers comprising free-radically polymerized units of 28 to 32% by weight of methyl methacrylate and 68 to 72% by weight of ethyl acrylate. The coating layer may comprise a (meth)acrylate copolymer comprising polymerized units of 60 to 80% of ethyl acrylate and 40 to 20% by weight of methyl methacrylate.

Preference is given to (meth)acrylate copolymers which, according to WO 01168767, have been prepared as dispersions using 1-10% by weight of a non-ionic emulsifier having an HLB value of 15.2 to 17.3. The latter offers the advantage that there is no phase separation with formation of crystal structures by the emulsifier (EUDRAGIT® NM type).

Preferably, the coating layer may comprise a mixture of a (meth)acrylate copolymer comprising polymerized units of 40 to 60% by weight of methacrylic acid and 60 to 40% by weight of ethyl acrylate and a (meth)acrylate copolymer comprising polymerized units of 60 to 80% of ethyl acrylate and 40 to 20% by weight of methyl methacrylate at a ratio from 10:1 to 1:10 by weight.

The coating layer may comprise a mixture of a (meth)acrylate copolymer of the above-mentioned types EUDRAGIT® FS and the type EUDRAGIT® L 100-55.

Preferably, the coating layer may comprise a mixture of a (meth)acrylate copolymer comprising polymerized units of 5 to 15% by weight methacrylic acid, 60 to 70% by weight of methyl acrylate and 20 to 30% by weight methyl methacrylate and a (meth)acrylate copolymer comprising polymerized units of 40 to 60% by weight of methacrylic acid and 60 to 40% by weight of ethyl acrylate at a ratio from 1:1 to 5:1 by weight.

The coating layer may also comprise a mixture of a (meth)acrylate copolymer(s) in the form of a core-shell polymer from two (meth)acrylate copolymer(s). The coating layer may comprise a (meth)acrylate copolymer which is a core-shell polymer, comprising 50 to 90, preferably 70 to 80% by weight of a core, comprising polymerized units of 60 to 80, preferably 65 to 75% by weight of ethyl acrylate and 40 to 20, preferably 35 to 25% by weight of methyl methacrylate, and 50 to 10, preferably 30 to 20% by weight of a shell, comprising polymerized units of 40 to 60, preferably 45 to 55% by weight of ethyl acrylate and 60 to 40, preferably 55 to 45% by weight of methacrylic acid.

A suitable core-shell polymer is EUDRAGIT® FL 30 D-55 (Evonik Nutrition & Care GmbH, Darmstadt, Germany), which is a commercially available 30% by weight aqueous dispersion of a copolymer from a two-stage emulsion polymerization process, with a core of about 75% by weight, comprising polymerized units of about 70% by weight of ethyl acrylate and 30% by weight of methyl methacrylate, and a shell of about 25% by weight, comprising polymerized units of 50% by weight ethyl acrylate and 50% by weight methacrylic acid. The glass transition temperature $T_{gm}$ of the polymer of EUDRAGIT® FL 30D-55 is about 8° C.

Pharmaceutical or Nutraceutical Excipients

Pharmaceutical or nutraceutical excipients are well known to a skilled person and often formulated along with the biologically active ingredient contained in the coated hard-shell capsule and/or with the polymer coating of the hard-shell capsule as disclosed herein. All pharmaceutical or nutraceutical excipients used must be toxicologically safe to be used in pharmaceuticals or nutraceuticals without risk for patients or consumers.

Pharmaceutically or nutraceutically acceptable excipients, may be selected from the group of antioxidants, brighteners, binding agents, flavouring agents, flow aids, fragrances, glidants, penetration-promoting agents, pigments, plasticizers, polysaccharide polymers, emulsifiers, pore-forming agents or stabilizers or combinations thereof. A pharmaceutically or nutraceutically acceptable excipient is an excipient, which is allowed to be used for the application in the pharmaceutical or nutraceutical field.

The pharmaceutical or nutraceutical excipients may preferably comprise one or more plasticizers and/or one or more detacking agents.

The addition of plasticizer(s) to the (meth)acrylate copolymer(s) is usually lowering the glass transition temperature of the mixture, elongation at break is usually increased. The effect may depend on the type and amount of plasticizer that is added. Plasticizer(s) may be selected from the groups of alkyl citrates, glycerol esters, alkyl phthalates, alkyl sebacates, sucrose esters, sorbitan esters, glycerol, propylene glycol and polyethylene glycols. Preferred plasticizers are triethyl citrate, polyethylene glycol 20,000 and propylene glycol. The amount of plasticizer added may be in the range of 2 to 50, preferably 5 to 30% by weight calculated on the weight of the (meth)acrylate copolymer(s).

The addition of detacking agents to the (meth)acrylate copolymer(s) is usually decreasing the tackiness of the mixture respectively of the coated film. Detacking agent(s) may be selected from Ca-stearate or Mg-stearate, glycerol monostearate and talc. The amount of detacking agent added may be in the range of 2 to 60, preferably 5 to 55% by weight calculated on the weight of the (meth)acrylate copolymer(s).

The coating layer may further comprise an emulsifier, preferably polysorbate 80. The amount of emulsifier added may be in the range of 1 to 30, preferably 3 to 25% by weight calculated on the weight of the (meth)acrylate copolymer(s).

Top Coat

The coating layer may comprise or include an additional top coat in an amount of 0.2 to 0.8 mg/cm$^2$, comprising hydroxypropyl methyl cellulose and optionally pigments or colorants. The top coat may also comprise further excipient polymers such as polyvinyl alcohol (PVA), hydroxy propyl cellulose (HPC) or Opadry. Preferably the top coat does not comprise essential amounts or no (meth)acrylate copolymer(s) at all.

Colon Delivery Combination

Especially for colon delivery, preference is given to the addition of an excipient polymer, which is polysaccharide polymer selected from the group consisting of starch, amylose, amylopectin, chitosan, chondroitin sulfate, cyclodextrin, dextran, pullulan, carrageenan, scleroglucan, chitin, curdulan and levan in coating layer comprising one or more (meth)acrylate copolymer(s) with a pH threshold at pH 5 or above (s. EP 2018159B1). The ratio of the polysaccharide polymer to the one or more (meth)acrylate copolymer(s) may be up to 50:50, preferably up to 35:65. (Meth)acrylate copolymers with a pH threshold at pH 5 are preferably of the type EUDRAGIT® L100 or EUDRAGIT® S, preferably used in combination with a starch comprising at least 35% by weight amylose. The pH threshold is the pH below which the one or more (meth)acrylate copolymer(s) are insoluble and at or above they are soluble in buffer, intestinal juice or simulated intestinal fluid.

Capsule Filling Machine

The polymer-coated hard-shell capsule is provided in the pre-locked state to a capsule-filling machine, which performs the steps of separating the body and the cap, filling the body with the fill and rejoining the body and the cap in the final-locked state.

The capsule filling machine used may be a capsule filling machine, preferably a fully automated capsule filling machine, that is capable to produce filled and closed capsules at a speed with an output of 1,000 or more filled and finally closed capsules per hour. Capsule filling machines, preferably fully automated capsule filling machines, are well known in the art and commercially available from several companies. A suitable capsule filling machine as used in the examples may be for instance ACG, model AFT Lab.

The capsule filling machine used may be preferably operated at a speed with an output of 1,000 or more, preferably 10,000 or more, 100,000 or more, 10,000 up to 500,000, filled and finally dosed capsules per hour.

Capsule Filling Machine General Operations

Before the capsule filling process, the capsule filling machine is provided with a sufficient number or amount of pre-coated hard-shell capsules in the pre-locked state. The capsule filling machine is also provided with sufficient amounts of fill to be filled in during operation.

The hard-shell capsules in the pre-locked state may fall by gravity into feeding tubes or chutes. The capsules may be uniformly aligned by mechanically gauging the diameter differences between the cap and the body. The hard-shell capsules are then usually fed, in proper orientation, into a two-section housing or brushing.

The diameter of the upper bushing or housing is usually larger than the diameter of the capsule body bushing; thus, the capsule cap may be retained within an upper bushing while the body is pulled into a lower bushing by vacuum. Once the capsule is opened/the body and the cap are separated, the upper and lower housing or bushing are separated to position the capsule body for filling.

The open capsule body is then filled with the fill. Various types of filling mechanisms may be applied, with respect to the different fillings such as granules, powders, pellets or mini-tablets. Capsule filling machines in general employ a variety of mechanisms to handle the various dosage ingredients as well as various numbers of filling stations. The dosing systems are usually based on volumetric or amounts of fills governed by the capsule size and capacity of the capsule body. The empty capsule manufacturers usually provide reference tables that indicate the volume capacity of their capsule body and the maximum fill weight for different capsule sizes based on the density of the fill material. After the filling, the body and the cap are rejoined by the machine in the final-locked state or position.

EXAMPLES

Elongation at break values of dried films corresponding to the composition of the coating layer of examples 1 to 7.

Elongation at break may be determined according to DIN EN ISO 527-3:2019-02, determination of tensile properties for plastic foils and sheets with a thickness below 1,000 µm. The elongation at break is the percentage increase in length that a material will achieve before breaking. This figure is shown as the percentage. Suspension of the compositions for the coating layer are spread on a glass plate and dried to a film of 250 µm thickness. The elongation at break is determined with these samples according to DIN EN ISO 527-3:2019-02.

Example for the preparation and testing of polymer films:
Formulation:
Polymer dispersion 30 g=9 g solids, used for a 250 µm film after drying.
Equipment:
Glass plate 20 cm×20 cm with a surrounding of 1 cm glass strips of 0.5-0.7 cm height, resulting in a free preparation area of 361 cm. This glass plate is in addition covered with a self-adhesive Polytetrafluoroethylen foil (i.e. Tygaflor®).
Processing:
The polymer and diluent are mixed on a magnetic stirrer for 10 minutes at low speed. The polymer solution or suspension needs to be air free to avoid voids in the polymer foil. The Polytetrafluoroethylen covered glass plate is levelled in an oven and the polymer solution or dispersion is poured into it. The mixture is dried for approximately 4 days at 40° C. After drying the foils or sheets will be conditioned for 16 hours at 23° C. and 50% relative humidity.

The resulting film thickness is approx. 250 µm.

The same method can be used to manufacture films of coating suspensions. In this case the coating suspension is prepared like usually (e.g. using an ultra turrax). An aliquot amount for 9 g of total solids (including formulation excipients) is diluted with demineralized water up to a total amount of 100 g.

Results

Example 1 (Inventive)—Enteric Coating/c EUDRAGIT® L 30D-65 and EUDRAGIT® NM 30D Combination on Pre-Locked Capsules in Drum Coater and Automatic Capsule Filling The EUDRAGIT® polymer(s) were mixed in a suitable sized container. The additional excipients were added into the water while gently stirring. After a suitable post stirring time the excipient suspension was added to the polymer dispersion. The spraying suspension was gently stirred during the coating process. The capsules were coated in the pre-locked state utilizing a drum coater.

TABLE 1

Formulation Example 1-Coating on Kcaps ® HPMC Size 0 capsules
(Batch size 90 g i.e. 833 capsules)

| Material | Composition | Solid Composition Percentage |
|---|---|---|
| EUDRAGIT ® L 30 D-55 | 2.7 mg/cm$^2$ | 75.0% |
| EUDRAGIT ® NM 30D | 0.3 mg/cm$^2$ | 8.33% |
| Triethyl citrate | 20% on ds* | 16.67% |
| Demineralized water | On demand | n/a |
| Solid content | 10% w/w | |
| Total solid weight gain | 3.6 mg/cm$^2$ | |

*Quantity based on dry polymer substance [%]

TABLE 2

Process Parameter Example 1

| Parameter | Value |
|---|---|
| Machine | Neocota 5D |
| Batch size [g] | 90 |
| Nozzle bore [mm] | 0.8 |
| Internal tube diameter [mm] | 3.0 |
| Peristaltic pump | Flowtech |
| Atomizing pressure [bar] | 1.5 |
| Flat pattern pressure [bar] | 0.5 |
| Room temperature [° C.] | 21-24 |
| Room humidity [% r.h.] | 50-55 |
| Pan speed [rpm] | 11 |
| Inlet air temperature [° C.] | 33-38 |
| Exhaust air temperature [° C.] | 28-31 |
| Product temperature [° C.] | 28-29 |

| Example | | Coating layer [mg/cm2] | Elongation at break [%] | Process |
|---|---|---|---|---|
| 1 | Inventive | 3.6 | ca. 70 | Pre-coated capsules, capsule filling machine |
| 2 | Comparative | 3.6 | ca. 70 | Uncoated capsules. capsule filling machine, post-coating |
| 3 | Comparative | 6.0 | ca. 70 | Pre-coated capsules, capsule filling machine |
| 4 | Inventive | 3.3 | ca. 30 | Pre-coated capsules, capsule filling machine |
| 5 | Comparative | 3.3 | ca. 30 | Uncoated capsules. capsule filling machine, post-coating |
| 6 | Inventive | 2.9 | ca. 70 | Pre-coated capsules, capsule filling machine |
| 7 | Comparative | 2.8 | ca. 5 | Pre-coated capsules, capsule filling machine |

TABLE 2-continued

Process Parameter Example 1

| Parameter | Value |
|---|---|
| Spray rate [g/min/kg] | 8-16 |
| Process time [min] | 190 |

Encapsulation Parameter 557 mg of Omeprazole pellets (5% Omeprazole) were filled into the polymer coated pre-locked capsules using an automatic Capsule filling equipment AFTLAB, ACG with a pellets filling set up using standard format size 0 tooling for capsule opening, transport, filling and closing. The machine output was set to 5,000-5,400 cps/hour.

Capsules tested in automatic capsule filling machine, 3.0 mg/cm polymer or 3.6 mg/cm$^2$ total solid weight gain feasible to process automatically. Capsule filling operation was smooth, capsules body and caps were easily opened and fit into the machine parts. Yield of 98% could be achieved (only 2% capsules were rejected by machine) on automatic capsule filling machine.

Dissolution Test

Method:

Apparatus: Labindia DS 8000 Paddle Apparatus (USP II) with sinkers

Detection method: HPLC analysis

Temperature: 37.5° C.

Media I: 500 ml 0.1 N HCL for 2 hours

Media II: 900 ml KH2PO4 pH 6.8 buffer for 1 hour

Paddle speed: 100 rpm

TABLE 3

Dissolution Results (n = 12) Example 1

| Media | Time [min] | Mean [% released] | SD |
|---|---|---|---|
| 0.1N HCL | 0 | 0.0 | 0.0 |
| 0.1N HCL | 120 | 2.8 | 1.8 |
| pH6.8 | 135 | 27.5 | 9.4 |
| pH6.8 | 150 | 89.0 | 10.2 |
| pH6.8 | 165 | 97.0 | 2.0 |
| pH6.8 | 180 | 95.7 | 1.5 |

Example 2 (Comparative)—Enteric Coating of EUDRAGIT® L 30D-65 and EUDRAGIT® NM 30D Combination on Filled and Locked Capsules (Omeprazole Pellets) in Drum Coater Encapsulation Parameter 590 mg of Omeprazole pellets (5% Omeprazole) were filled into the Kcaps HPMC Size 0 capsules using an automatic Capsule filling equipment AFTLAB, ACG with a pellets filling set up using standard format size 0 tooling for capsule opening, transport, filling and dosing. The machine output was set to 5,000-5,400 cps/hour.

Capsule filling operation was smooth, capsules body and caps were easily opened and fit into the machine parts. Yield of 99.7% could be achieved (only 0.3% capsules were rejected by machine) on automatic capsule filling machine.

Enteric coating on Omeprazole filled capsules:

The EUDRAGIT® polymer(s) were mixed in a suitable sized container. The additional excipients were added into the water while gently stirring. After a suitable post stirring time the excipient suspension was added to the polymer dispersion. The spraying suspension was gently stirred during the coating process. The omeprazole filled capsules were then coated in the locked state utilizing a drum coater.

TABLE 4

Formulation Example 2-Coating on Omeprazole filled Kcaps ® HPMC Size 0 capsules (Batch size 550 g i.e 833 capsules)

| Material | Composition | Solid Composition Percentage |
|---|---|---|
| EUDRAGIT ® L 30 D-55 | 2.7 mg/cm$^2$ | 75.0% |
| EUDRAGIT ® NM 30D | 0.3 mg/cm$^2$ | 8.33% |
| Triethyl citrate | 20% on ds* | 16.67% |
| Demineralized water | On demand | n/a |
| Solid content | 10% w/w | |
| Total solid weight gain | 3.6 mg/cm$^2$ | |

*Quantity based on dry polymer substance [%]

TABLE 5

Process Parameter Example 2

| Parameter | Value |
|---|---|
| Machine | Neocota 5D |
| Batch size [g] | 550 |
| Nozzle bore [mm] | 0.8 |
| Internal tube diameter [mm] | 3.0 |
| Peristaltic pump | Flowtech |
| Atomizing pressure [bar] | 1.5 |
| Flat pattern pressure [bar] | 0.5 |
| Room temperature [° C.] | 21-24 |
| Room humidity [% r.h.] | 50-55 |
| Pan speed [rpm] | 11 |
| Inlet air temperature [° C.] | 35-38 |
| Exhaust air temperature [° C.] | 29-30 |
| Product temperature [° C.] | 28-29 |
| Spray rate [g/min/kg] | 1.36-2.72 |
| Process time [min] | 120 |

Dissolution Test

Method:

Apparatus: Labindia DS 8000 Paddle Apparatus (USP II) with sinkers

Detection method: HPLC analysis

Temperature: 37.5° C.

Media I: 500 ml 0.1 N HCL

Paddle speed: 100 rpm

TABLE 6

Dissolution Results (n = 12) Example 1

| Media | Time [min] | Mean [% released] | SD |
|---|---|---|---|
| 0.1N HCL | 0 | 0.0 | 0.0 |
| 0.1N HCL | 120 | 25.8 | 20.4 |

Dissolution testing of Example-2 was only carried out in the 0.1N HCl for 2 hours because Acid release/degradation of Omeprazole observed after 2 hours exposure to 0.1N HCl. At same coating build up enteric polymer coating on filled and locked capsules failed to give acid resistance as compared to coating on Pre-locked capsules followed by filling (Example-1).

Example 3 (Comparative)—Enteric Coating of EUDRAGIT® L 30D-65 and EUDRAGIT® NM 30D Combination on Pre-Locked Capsules in Drum Coater and Automatic Capsule Filling The EUDRAGIT® polymer (s) were mixed in a suitable sized container. The additional excipients were added into the water while gently stirring. After a suitable post sting time the excipient suspension was added to the polymer dispersion. The spraying suspension was gently stirred during the coating process. The capsules were coated in the pre-locked state utilizing a drum coater.

TABLE 7

Formulation Example 3-Coating on Kcaps ® HPMC Size 0 capsules (Batch size 90 g i.e. 833 capsules)

| Material | Composition | Solid Composition Percentage |
|---|---|---|
| EUDRAGIT ® L 30 D-55 | 4.5 mg/cm$^2$ | 75.0% |
| EUDRAGIT ® NM 30D | 0.5 mg/cm$^2$ | 8.33% |
| Triethyl citrate | 20% on ds* | 16.67% |
| Demineralized water | On demand | n/a |
| Solid content | 10% w/w | |
| Total solid weight gain | 6 mg/cm$^2$ | |

*Quantity based on dry polymer substance [%]

TABLE 8

Process Parameter Example 3

| Parameter | Value |
|---|---|
| Machine | Neocota 5D |
| Batch size [g] | 90 |
| Nozzle bore [mm] | 0.8 |
| Internal tube diameter [mm] | 3.0 |
| Peristaltic pump | Flowtech |
| Atomizing pressure [bar] | 1.5 |
| Flat pattern pressure [bar] | 0.5 |
| Room temperature [° C.] | 21-24 |
| Room humidity [% r.h.] | 50-55 |
| Pan speed [rpm] | 11 |
| Inlet air temperature [° C.] | 32-38 |
| Exhaust air temperature [° C.] | 28-32 |
| Product temperature [° C.] | 28-30 |
| Spray rate [g/min/kg] | 8-16 |
| Process time [min] | 375 |

Encapsulation Parameter 595 mg of Omeprazole pellets (5% Omeprazole) was filled into the polymer coated pre-locked capsules using an automatic Capsule filling equipment AFTLAB, ACG with a pellets filling set up using standard format size 0 tooling for capsule opening, transport, filling and closing. The machine output was set to 1,000-1,200 cps/hour.

Capsules tested in automatic capsule filling machine. At 5.0 mg/cm$^2$ polymer or 6.0 mg/cm$^2$ total solid weight gain the limitation was the standard tooling which was not able to operate with the pre-locked capsules due to the increased layer thickness. Capsule filling operation was not smooth, capsules body and caps were easily opened but failed to fit into the machine parts due to increase in the coating thickness. Yield of only 67% could be achieved and 33% capsules were rejected by the machine. Due to high rejection rate the filled capsules were not analyzed for dissolution testing.

Example 4 (Inventive)—Enteric Coating 8. EUDRAGIT® FS 30D and EUDRAGIT® L 30D-65 Combination on Pre-Locked Capsules in Drum Coater and Automatic Capsule Filling The EUDRAGIT® polymer(s) were mixed in a suitable sized container. The additional excipients were added into the water while gently stirring. After a suitable post stirring time the excipient suspension was added to the polymer dispersion. The spraying suspension was gently stirred during the coating process. The capsules were coated in the pre-locked state utilizing a drum coater.

TABLE 9

Formulation Example 4-Coating on Kcaps ® HPMC Size 0 capsules (Batch size 90 g i.e. 833 capsules)

| Material | Composition | Solid Composition Percentage |
|---|---|---|
| EUDRAGIT ® FS 30D | 2.25 mg/cm$^2$ | 68.18% |
| EUDRAGIT ® L 30 D-55 | 0.75 mg/cm$^2$ | 22.73% |
| Triethyl citrate | 10% on ds* | 9.09% |
| Demineralized water | On demand | n/a |
| Solid content | 10% w/w | |
| Total solid weight gain | 3.3 mg/cm$^2$ | |

*Quantity based on dry polymer substance [%]

TABLE 10

Process Parameter Example 4

| Parameter | Value |
|---|---|
| Machine | Neocota 5D |
| Batch size [g] | 90 |
| Nozzle bore [mm] | 0.8 |
| Internal tube diameter [mm] | 3.0 |
| Peristaltic pump | Flowtech |
| Atomizing pressure [bar] | 1.5 |
| Flat pattern pressure [bar] | 0.5 |
| Room temperature [° C.] | 21-24 |
| Room humidity [% r.h.] | 50-55 |
| Pan speed [rpm] | 11 |
| Inlet air temperature [° C.] | 36-38 |
| Exhaust air temperature [° C.] | 28-29 |
| Product temperature [° C.] | 28-29 |
| Spray rate [g/min/kg] | 8 |
| Process time [min] | 240 |

Encapsulation Parameter 525 mg of Metoprolol pellets (40% Metoprolol) were filled into the polymer coated pre-locked capsules using an automatic Capsule filling equipment AFTLAB, ACG with a pellets filling set up using standard format size 0 tooling for capsule opening, transport, filling and closing. The machine output was set to 5,000-5,400 cps/hour.

Capsules tested in automatic capsule filling machine, 3.0 mg/cm polymer or 3.3 mg/cm$^2$ total solid weight gain feasible to process automatically. Capsule filling operation was smooth, capsules body and caps were easily opened and fit into the machine parts. Yield of 97% could be achieved (only 3% capsules were rejected by machine) on automatic capsule filling machine.

Dissolution Test

Method:

Apparatus: Labindia DS 8000 Paddle Apparatus (USP II) with sinkers

Detection method: HPLC analysis

Temperature: 37.5° C.

Media I: 500 ml 0.1 N HCL for 2 hours

Media II: 900 ml KH2PO4 pH 6.8 buffer for 1 hour

Media III: 900 ml KH2PO4 pH 7.4 buffer for 2 hours

Paddle speed: 100(media1)/100(media2)/50(media3)

TABLE 11

Dissolution Results (n = 12) Example 4

| Media | Time [min] | Mean [% released] | SD |
|---|---|---|---|
| 0.1N HCL | 0 | 0.00 | 0.00 |
| 0.1N HCL | 120 | 0.18 | 0.34 |
| pH6.8 | 180 | 14.56 | 19.77 |
| pH7.4 | 195 | 34.89 | 20.80 |
| pH7.4 | 210 | 54.54 | 15.56 |
| pH7.4 | 225 | 71.56 | 9.94 |
| pH7.4 | 240 | 83.58 | 7.44 |
| pH7.4 | 270 | 90.44 | 6.71 |
| pH7.4 | 300 | 91.30 | 7.84 |

Example 5 (Comparative)—Enteric Coating of EUDRAGIT® FS 30D and EUDRAGIT® L 30D-65 Combination on Filled and Locked Capsules (Metoprolol Pellets) in Drum Coater Encapsulation Parameter 517 mg of Metoprolol pellets (40% Metoprolol) were filled into the Kcaps HPMC Size 0 capsules using an automatic Capsule filling equipment AFTLAB, ACG with a pellets filling set up using standard format size 0 tooling for capsule opening, transport, filling and dosing. The machine output was set to 5,000-5,400 cps/hour.

Capsule filling operation was smooth, capsules body and caps were easily opened and fit into the machine parts. Yield of 100% could be achieved on automatic capsule filling machine.

Enteric Coating on Metoprolol Filled Capsules:

The EUDRAGIT® polymer(s) were mixed in a suitable sized container. The additional excipients were added into the water while gently stirring. After a suitable post stirring time the excipient suspension was added to the polymer dispersion. The spraying suspension was gently stirred during the coating process. The Metoprolol filled capsules were then coated in the locked state utilizing a drum coater.

TABLE 12

Formulation Example 5-Coating on Metoprolol filled Kcaps ® HPMC Size 0 capsules (Batch size 550 g i.e 833 capsules)

| Material | Composition | Solid Composition Percentage |
|---|---|---|
| EUDRAGIT ® FS 30D | 2.25 mg/cm² | 68.18% |
| EUDRAGIT ® L 30 D-55 | 0.75 mg/cm² | 22.73% |
| Triethyl citrate | 10% on ds* | 9.09% |
| Demineralized water | On demand | n/a |
| Solid content | 10% w/w | |
| Total solid weight gain | 3.3 mg/cm² | |

*Quantity based on dry polymer substance [%]

TABLE 13

Process Parameter Example 5

| Parameter | Value |
|---|---|
| Machine | Neocota 5D |
| Batch size [g] | 550 |
| Nozzle bore [mm] | 0.8 |
| Internal tube diameter [mm] | 3.0 |
| Peristaltic pump | Flowtech |
| Atomizing pressure [bar] | 1.5 |
| Flat pattern pressure [bar] | 0.5 |
| Room temperature [° C.] | 21-24 |
| Room humidity [% r.h.] | 50-55 |
| Pan speed [rpm] | 11 |
| Inlet air temperature [° C.] | 36-38 |
| Exhaust air temperature [° C.] | 28-30 |
| Product temperature [° C.] | 28-29 |
| Spray rate [g/min/kg] | 1.36-2.72 |
| Process time [min] | 140 |

Dissolution Test

Method:

Apparatus: Labindia DS 8000 Paddle Apparatus (USP II) with sinkers

Detection method: HPLC analysis

Temperature: 37.5° C.

Media I: 500 ml 0.1 N HCL for 2 hours

Media II: 900 ml KH2PO4 pH 6.8 buffer for 1 hour

Media III: 900 ml KH2PO4 pH 7.4 buffer for 2 hours

Paddle speed: 100(media1)/100(media2)/50(media3)

TABLE 14

Dissolution Results (n = 12) Example 5

| Media | Time [min] | Mean [% released] | SD |
|---|---|---|---|
| 0.1N HCL | 0 | 0.0 | 0.0 |
| 0.1N HCL | 120 | 27.3 | 40.6 |
| pH6.8 | 180 | 84.9 | 16.0 |

Dissolution testing of Example-5 was only carried out in the 0.1N HCl for 2 hours and pH 6.8 buffer for 1 hour because complete release of Metoprolol observed in pH 6.8 buffer. At same coating build up enteric polymer coating on filled and locked capsules failed to give acid resistance as compared to coating on Pre-locked capsules followed by filling (Example-4).

Example 6 (Inventive)—Enteric Coating of EUDRAGIT® L 30D-65 and EUDRAGIT® NM 30D Combination on Pre-Locked Capsules Followed by Top Coat of HPMC in Drum Coater and Automatic Capsule Filling The EUDRAGIT® polymer(s) were mixed in a suitable sized container. The additional excipients were added into the water while gently stirring. After a suitable post stirring time the excipient suspension was added to the polymer dispersion. The spraying suspension was gently stirred during the coating process. The capsules were coated in the pre-locked state utilizing a drum coater. Top coat: HPMC was dissolved in water under stirring and sprayed on to the coated capsules utilizing a drum coater.

TABLE 15

Formulation Example 6-Coating on Kcaps ® HPMC Size 0 capsules
(Batch size 500 g i.e. 4595 capsules)

| Coating | Material | Composition | Solid Composition Percentage |
|---|---|---|---|
| Functional coat | EUDRAGIT ® L 30 D-55 | 1.8 mg/cm$^2$ | 75.0% |
|  | EUDRAGIT ® NM 30D | 0.2 mg/cm$^2$ | 8.33% |
|  | Triethyl citrate | 20% on ds* | 16.67% |
|  | Demineralized water | On demand | n/a |
|  | Solid content | 10% w/w |  |
|  | Total solid weight gain | 2.4 mg/cm$^2$ |  |
| Top coat | HPMC 3 cps | 0.5 mg/cm$^2$ | 100% |
|  | Demineralized water | On demand | n/a |
|  | Solid content | 5% w/w |  |
|  | Total solid weight gain | 0.5 mg/cm$^2$ |  |

*Quantity based on dry polymer substance [%]

TABLE 16

Process Parameter Example 6

| Parameter | Value Functional coat (EUDRAGIT ®) | Value Top coat (HPMC) |
|---|---|---|
| Machine | Neocota 5D | Neocota 5D |
| Batch size [g] | 500 | 559 |
| Nozzle bore [mm] | 0.8 | 0.8 |
| Internal tube diameter [mm] | 3.0 | 3.0 |
| Peristaltic pump | Flowtech | Flowtech |
| Atomizing pressure [bar] | 1.5 | 1.5 |
| Flat pattern pressure [bar] | 1.0 | 1.0 |
| Room temperature [° C.] | 21-24 | 21-24 |
| Room humidity [% r.h.] | 50-55 | 50-55 |
| Pan speed [rpm] | 8 | 8 |
| Inlet air temperature [° C.] | 50-58 | 38-40 |
| Exhaust air temperature [° C.] | 28-31 | 29-31 |
| Product temperature [° C.] | 27-29 | 28-29 |
| Spray rate [g/min/kg] | 4.5-18 | 6.70-10.7 |
| Process time [min] | 105 | 60 |

Encapsulation Parameter 590 mg of Omeprazole pellets (5% Omeprazole) were filled into the polymer coated pre-locked capsules using an automatic Capsule filling equipment AFTLAB, ACG with a pellets filling set up using standard format size 0 tooling for capsule opening, transport, filling and closing. The machine output was set to 5,000-5,400 cps/hour.

Capsules tested in automatic capsule filling machine, 2.5 (2.0 EUDRAGIT+0.5 HPMC) mg/cm polymer or 2.9 (2.4 EUDRAGIT+0.5 HPMC) mg/cm$^2$ solid weight gain feasible to process automatically. Capsule filling operation was smooth, capsules body and caps were easily opened and fit into the machine parts. Yield of 95% could be achieved (only 5% capsules were rejected by machine) on automatic capsule filling machine.

Dissolution Test

Method:

Apparatus: Labindia DS 8000 Paddle Apparatus (USP II) with sinkers

Detection method: HPLC analysis

Temperature: 37.5° C.

Media I: 500 ml 0.1 N HCL for 2 hours

Media II: 900 ml KH2PO4 pH 6.8 buffer for 1 hour

Paddle speed: 100 rpm

TABLE 17

Dissolution Results (n = 6) Example 1

| Media | Time [min] | Mean [% released] | SD |
|---|---|---|---|
| 0.1N HCL | 0 | 0.0 | 0.0 |
| 0.1N HCL | 120 | 1.7 | 0.6 |
| pH6.8 | 135 | 43.7 | 10.8 |
| pH6.8 | 150 | 91.6 | 7.1 |
| pH6.8 | 165 | 94.4 | 1.4 |
| pH6.8 | 180 | 93.3 | 1.3 |

Comparative Example 7—Enteric Coating of Standard EUDRAGIT® L 30D-65 Coating with Glycerol Mono Stearate (GMS) on Pre-Locked Capsules Followed by Top Coat of HPMC in Drum Coater and Automatic Capsule Filling GMS emulsion was prepared by adding Polysorbate 80 (33% solution), Triethyl citrate and GMS in hot water (70-80° C.) under high shear homogenizer for 10 minutes. Prepared GMS emulsion was allowed to cool down at room temperature and then added to EUDRAGIT® polymer dispersion under overhead stirring. The spraying suspension was gently stirred during the coating process. The capsules were coated in the pre-locked state utilizing a drum coater. Top coat: HPMC was dissolved in water under stirring and sprayed on to the coated capsules utilizing a drum coater.

TABLE 18

Formulation Example 7-Coating on Kcaps ® HPMC Size 0 capsules
(Batch size 90 g i.e. 833 capsules)

| Coating | Material | Composition | Solid Composition Percentage |
|---|---|---|---|
| Functional coat | EUDRAGIT ® L 30 D-55 | 2 mg/cm$^2$ | 85.47% |
|  | Polysorbate 80 (33% solution) | 2% on ds* | 1.71% |
|  | Triethyl citrate | 10% on ds* | 8.55% |
|  | Glycerol mono stearate | 5% on ds* | 4.27% |
|  | Demineralized water | On demand | n/a |
|  | Solid content | 10% w/w |  |
|  | Total solid weight gain | 2.34 mg/cm$^2$ |  |
| Top coat | HPMC 3 cps | 0.5 mg/cm$^2$ | 100% |
|  | Demineralized water | On demand | n/a |
|  | Solid content | 5% w/w |  |
|  | Total solid weight gain | 0.5 mg/cm$^2$ |  |

*Quantity based on dry polymer substance [%]

TABLE 19

Process Parameter Example 7

| Parameter | Value Functional coat (EUDRAGIT ®) | Value Top coat (HPMC) |
|---|---|---|
| Machine | Neocota 5D | Neocota 5D |
| Batch size [g] | 90 | 100 |
| Nozzle bore [mm] | 0.8 | 0.8 |
| Internal tube diameter [mm] | 3.0 | 3.0 |
| Peristaltic pump | Flowtech | Flowtech |
| Atomizing pressure [bar] | 1.5 | 1.5 |
| Flat pattern pressure [bar] | 0.5 | 0.5 |
| Room temperature [° C.] | 21-24 | 21-24 |
| Room humidity [% r.h.] | 50-55 | 50-55 |
| Pan speed [rpm] | 11 | 11 |
| Inlet air temperature [° C.] | 34-36 | 36-37 |

TABLE 19-continued

Process Parameter Example 7

| Parameter | Value Functional coat (EUDRAGIT ®) | Value Top coat (HPMC) |
|---|---|---|
| Exhaust air temperature [° C.] | 27-31 | 30-31 |
| Product temperature [° C.] | 27-29 | 28-29 |
| Spray rate [g/min/kg] | 8.33-16.66 | 8.33-16.66 |
| Process time [min] | 120 | 30 |

Encapsulation Parameter 590 mg of Omeprazole pellets (5% Omeprazole) were filled into the polymer coated pre-locked capsules using an automatic Capsule filling equipment AFTLAB, ACG with a pellets filling set up using standard format size 0 tooling for capsule opening, transport, filling and dosing. The machine output was set to 5,000-5,400 cps/hour.

Capsules tested in automatic capsule filling machine, 2.5 (2.0 EUDRAGIT+0.5 HPMC) mg/cm$^2$ polymer or 2.85 (2.35 EUDRAGIT+0.5 HPMC) mg/cm$^2$ solid weight gain feasible to process automatically. Capsule filling operation was smooth, capsules body and caps were easily opened and fit into the machine parts. Yield of 98.36% could be achieved (only 1.6% capsules were rejected by machine) on automatic capsule filling machine.

Dissolution Test

Method:

Apparatus: Labindia DS 8000 Paddle Apparatus (USP II) with sinkers
Detection method: HPLC analysis
Temperature: 37.5° C.
Media I: 500 ml 0.1 N HCL for 2 hours
Media II: 900 ml KH2PO4 pH 6.8 buffer for 1 hour
Paddle speed: 100 rpm

TABLE 20

| Dissolution Results (n = 6) Example 1 | | | |
|---|---|---|---|
| Media | Time [min] | Mean [% released] | SD |
| 0.1N HCL | 0 | 0.00 | 0.00 |
| 0.1N HCL | 120 | 11.02 | 3.16 |
| pH6.8 | 135 | 43.63 | 17.04 |
| pH6.8 | 150 | 86.71 | 11.45 |
| pH6.8 | 165 | 90.61 | 14.95 |
| pH6.8 | 180 | 94.22 | 7.95 |

Example 6—Determination of Capsule Overlap

Dimensions and tolerances of different commercially available capsules with respect to mean difference between pre-locked and locked lengths.

TABLE 21

| Hard-shell Capsule Dimensions (1/2) | | | | | | | | | |
|---|---|---|---|---|---|---|---|---|---|
| Manufacturer | Capsugel | | | Capsugel | | | Capsugel | | |
| Color | Transparent | | | White | | | Transparent | | |
| Size | #0 Vcaps ® plus | | | #0 Vcaps ® plus | | | #1 Vcaps ® plus | | |
| Locking stage | Unlocked | prelocked | Final-Locked | Unlocked | prelocked | Final Locked | Unlocked | prelocked | Final Locked |
| Length [mm] | 29.16 | 23.65 | 21.38 | 29.16 | 23.76 | 20.91 | 26.39 | 21.19 | 19.03 |
| SD [mm] | | 0.19 | 0.2 | | 0.16 | 0.17 | | 0.15 | 0.07 |
| Minimum [mm] | | 23.25 | 21 | | 23.43 | 20.67 | | 20.95 | 18.9 |
| Maximum [mm] | | 23.95 | 21.7 | | 23.99 | 21.31 | | 21.4 | 19.15 |
| Overlap length [mm] | | 5.51 | 2.27 | | 5.4 | 2.85 | | 5.2 | 2.16 |
| Total Overlap length [mm] | | 7.78 | | | 8.25 | | | 7.36 | |
| Overlap level | | 71% | 100% | | 65% | 100% | | 71% | 100% |

TABLE 22

| Hard-shell Capsule Dimensions (2/2) | | | | | | | | | |
|---|---|---|---|---|---|---|---|---|---|
| Manufacturer | Capsugel | | | ACG | | | ACG | | |
| Color | Transparent | | | Transparent | | | White | | |
| Size | #3 Vcaps ® plus | | | #0 Naturecaps | | | #0EL Naturecaps | | |
| Locking stage | Unlocked | prelocked | Final Locked | Unlocked | prelocked | Final Locked | Unlocked | prelocked | Final Locked |
| Length [mm] | 21.67 | 17.69 | 15.74 | 29.2 | 23.04 | 20.92 | 32 | 25.17 | 22.87 |
| SD [mm] | | 0.16 | 0.17 | | 0.12 | 0.16 | | 0.07 | 0.17 |
| Minimum [mm] | | 17.39 | 15.23 | | 22.65 | 20.68 | | 25.01 | 22.59 |
| Maximum [mm] | | 17.94 | 15.98 | | 23.21 | 21.22 | | 25.29 | 23.1 |
| Overlap length [mm] | | 3.98 | 1.95 | | 6.16 | 2.12 | | 6.83 | 2.3 |
| Total Overlap [mm] | | 5.93 | | | 8.28 | | | 9.13 | |
| Overlap level | | 67% | 100% | | 74% | 100% | | 75% | 100% |

Example 9—Surface Area Calculation and Colon Targeting Coating of Pre-Locked Capsules in Drum Coater Since a certain coating layer thickness is required to achieve the desired film functionality, the required amount of coating material depends on the surface area of the substrate. For this reason coating quantities are expressed as mg of total dry substance per cm² of substrate surface area. Below the equation of pre-locked capsule surface are is described considering the mean difference between the pre-locked state and the accumulated length of the separate capsule halves, body and cap.

$$A_{\frac{1}{2}Sphere} = 2\left(\frac{d}{2}\right)^2 \pi$$

$$A_{Cylinder, body} = 2\pi\left(\frac{d}{2}\right)(h - h_{overlap})$$

$$A_{Cylinder, body} = 2\pi\left(\frac{d}{2}\right)h$$

$$A_{Capsule-segment} = A_{\frac{1}{2}Sphere} + A_{Cylinder}$$

$$A_{Pre-locked\ capsule} = A_{Body} + A_{Cylinder}$$

A=Surface Area
h=Length
d=Diameter

Calculation Example 9 for the Calculation of the Outer Capsule Surface in the Pre-Locked State

TABLE 23

Vcaps ® Plus Capsule Specifications:

| Size | 00el | 00 | 0el | 0 | 1 | 1el | 2 | 3 | 4 |
|---|---|---|---|---|---|---|---|---|---|
| Weight | | | | | | | | | |
| Weight [mg] | 130 | 122 | 107 | 96 | 76 | 81 | 61 | 47 | 38 |
| Tolerance [mg] | ±10 | ±7 | ±7 | ±6 | ±5 | ±5 | ±4 | ±3 | ±3 |
| Length of the capsules halves (body and cap) | | | | | | | | | |
| Body [mm] | 22.20 | 20.22 | 20.19 | 18.44 | 16.61 | 17.70 | 15.27 | 13.59 | 12.19 |
| Tolerance [mm] | ±0.46 | ±0.46 | ±0.46 | ±0.46 | ±0.46 | ±0.46 | ±0.46 | ±0.46 | ±0.46 |
| Cap [mm] | 12.95 | 11.74 | 11.68 | 10.72 | 9.78 | 10.49 | 8.94 | 8.08 | 7.21 |
| Tolerance [mm] | ±0.46 | ±0.46 | ±0.46 | ±0.46 | ±0.46 | ±0.46 | ±0.46 | ±0.46 | ±0.46 |
| External diameter | | | | | | | | | |
| Body [mm] | 8.18 | 8.18 | 7.34 | 7.34 | 6.63 | 6.63 | 6.07 | 5.57 | 5.05 |
| Cap [mm] | 8.53 | 8.53 | 7.65 | 7.64 | 6.91 | 6.91 | 6.35 | 5.82 | 5.32 |
| Overall length in the final-locked state | | | | | | | | | |
| Length [mm] | 25.3 | 23.30 | 23.5 | 21.70 | 19.40 | 20.40 | 18.00 | 15.90 | 14.30 |
| Tolerance [mm] | ±0.30 | ±0.30 | ±0.30 | ±0.30 | ±0.30 | ±0.30 | ±0.30 | ±0.30 | ±0.30 |

FIG. 1/1 shows a schematic drawing of the body (left) and the cap (right) of a Vcaps® Plus size 1 hard-shell capsule with the relevant dimensions in mm. The dimensions are used in the calculation example 9 for the calculation of the outer capsule surface in the pre-locked state. The dimensions are:

Body: length=16.61 mm, cylinder (length of the cylindrical part)=13.29 mm, outer diameter=6.63 mm Cap: length=9.78 mm, cylinder (length of the cylindrical part)=6.32 mm, outer diameter=6.91 mm $$A_{\frac{1}{2}Sphere, Body} = 2\left(\frac{6.63}{2}\right)^2 \pi = 69.05 [mm^2]$$

$$A_{Cylinder, Body} = 2\pi\left(\frac{6.63}{2}\right)(13.29 - 5.2) = 168.50 [mm^2]$$

$$A_{\frac{1}{2}Sphere, Cap} = 2\left(\frac{6.91}{2}\right)^2 \pi = 75.00 [mm^2]$$

$$A_{Cylinder, Cap} = 2\pi\left(\frac{6.91}{2}\right)6.32 = 137.20 [mm^2]$$

$$A_{Capsule-body} = 69.05 + 168.50 = 237.55 [mm^2]$$

$$A_{Capsule-cap} = 75.00 + 137.20 = 212.20 [mm^2]$$

$$A_{Pre-locked\ capsule} = 237.55 + 212.20 = 449.75 [mm^2]$$

TABLE 24

Capsuls Surface Area

| Parameter | Body | Cap |
|---|---|---|
| $A_{1/2\ Sphere}$ [mm²] | 69.05 | 75.00 |
| $A_{Cylinder}$ [mm²] | 168.50 | 137.20 |
| $A_{Segment}$ [mm²] | 237.55 | 212.20 |
| $A_{Pre-locked\ capsule}$ [mm²] | | 449.75 |

The invention claimed is:

1. A process for preparing a polymer coated hard-shell capsule filled with a fill comprising a biologically active ingredient, the process comprising:

(a) preparing the polymer coated hard-shell capsule comprising:
a body and a cap both comprising a material selected from the group consisting of an ethyl ether of cellulose, methyl ether of cellulose, propyl ether of cellulose, starch, and pullulan; and
a coating layer present in an amount of 1-5.8 mg/cm², covering said capsule in the pre-locked state and comprising: (i) a (meth)acrylate copolymer having a glass transition temperature from −10° C. to 115° C. and selected from the group consisting of a copolymer of methacrylic acid and ethyl acrylate; a copolymer of methacrylic acid and methyl methacrylate; a copolymer of ethyl acrylate and methyl methacrylate; a copolymer of methacrylic acid, methyl acrylate, and methyl methacrylate; a mixture of a copolymer of methacrylic acid and ethyl acrylate with a copolymer of methyl methacrylate and ethyl acrylate; and a mixture of a copolymer of methacrylic acid, methyl acrylate, and methyl methacrylate with a copolymer of methyl methacrylate and ethyl acrylate; and (ii) 2-50 wt % of a plasticizer based on a weight of the dry (meth)acrylate copolymer, wherein the plasticizer is selected from the group consisting of an alkyl citrate, a glycerol ester, an alkyl phthalate, an alkyl sebacate, a sucrose ester, a sorbitan ester, a glycerol, a propylene glycol, and a polyethylene glycol; and wherein a dried film of the coating composition having a thickness of 250 µm has an elongation at break of 15-500%;

(b) providing said polymer coated hard-shell capsule, comprising a body and a cap in a pre-locked state, to a capsule filling machine;

(c) separating the body and the cap;

(d) filling the body with the fill comprising a biologically active ingredient, and rejoining the body and the cap in a final-locked state; wherein in a closed state the cap overlaps the body either in a pre-locked state or in a final-locked state.

2. The process according to claim 1, wherein the material of the body and the cap comprises hydroxypropyl methyl cellulose.

3. The process according to claim 1, wherein the coating layer comprises a (meth)acrylate copolymer comprising polymerized units of 40 to 60% by weight of methacrylic acid and 60 to 40% by weight of ethyl acrylate.

4. The process according to claim 1, wherein the coating layer comprises a (meth)acrylate copolymer comprising polymerized units of 60 to 80% by weight of ethyl acrylate and 40 to 20% by weight of methyl methacrylate.

5. The process according to claim 1, wherein the coating layer comprises a (meth)acrylate copolymer comprising polymerized units of 5 to 15% by weight of methacrylic acid, 60 to 70% by weight of methyl acrylate, and 20 to 30% by weight of methyl methacrylate.

6. The process according to claim 1, wherein the coating layer comprises a mixture of (meth)acrylate copolymers comprising polymerized units of 40 to 60% by weight of methacrylic acid and 60 to 40% by weight of ethyl acrylate, and a (meth)acrylate copolymer comprising polymerized units of 60 to 80% by weight of ethyl acrylate and 40 to 20% by weight of methyl methacrylate, at a ratio from 10:1 to 1:10 by weight.

7. The process according to claim 1, wherein the coating layer comprises a mixture of (meth)acrylate copolymers comprising polymerized units of 5 to 15% by weight of methacrylic acid, 60 to 70% by weight of methyl acrylate and 20 to 30% by weight of methyl methacrylate, and a (meth)acrylate copolymer comprising polymerized units of 40 to 60% by weight of methacrylic acid and 60 to 40% by weight of ethyl acrylate, at a ratio from 1:1 to 5:1 by weight.

8. The process according to claim 1, wherein the coating layer comprises 50 to 100% by weight of the one or more (meth)acrylate copolymer(s) and 50 to 0% by weight of pharmaceutical or nutraceutical excipients.

9. The process according to claim 8, wherein the pharmaceutical or nutraceutical excipients comprise one or more detacking agents.

10. The process according to claim 9, wherein the one or more detacking agents is/are selected from the group consisting of Ca-stearate, Mg-stearate, glycerol monostearate, and talc.

11. The process according to claim 1, wherein the capsule filling machine is operated at a speed with an output of 1,000 or more filled and finally closed capsules per hour.

12. The process according to claim 1, wherein the coating layer further comprises an emulsifier.

13. A hard-shell capsule, obtained by the process according to claim 1.

14. The process according to claim 12, wherein the emulsifier is polysorbate 80.

* * * * *